United States Patent [19]

Jones

[11] Patent Number: 4,499,053
[45] Date of Patent: Feb. 12, 1985

[54] FLUID SAMPLING

[75] Inventor: Ronald L. Jones, Harvard, Mass.

[73] Assignee: Instrumentation Laboratory Inc., Lexington, Mass.

[21] Appl. No.: 386,892

[22] Filed: Jun. 10, 1982

[51] Int. Cl.³ .............................................. G01N 1/14
[52] U.S. Cl. .................................. 422/68; 73/864.25; 422/50; 422/81
[58] Field of Search .......... 73/864.21, 864.22, 864.24, 73/864.25; 141/130; 422/63–66, 68, 100, 81; 436/54, 180

[56] References Cited

U.S. PATENT DOCUMENTS

| | | | |
|---|---|---|---|
| 3,748,911 | 7/1978 | Rousselet et al. ................ | 73/423 A |
| 3,842,680 | 10/1974 | Vollick et al. ..................... | 73/425.4 |
| 3,858,450 | 1/1975 | Jones ..................................... | 73/423 |
| 3,881,872 | 5/1975 | Naono ................................... | 23/253 |
| 3,912,456 | 10/1975 | Young ................................... | 23/253 |
| 3,949,615 | 4/1976 | Stein et al. ............................ | 73/423 |
| 3,963,440 | 6/1976 | Stein et al. ............................ | 23/253 |
| 4,000,973 | 1/1977 | Petersen ................................. | 23/230 |
| 4,046,511 | 9/1977 | Stabile ................................... | 23/259 |
| 4,054,415 | 10/1977 | Seligson et al. ....................... | 23/253 |
| 4,076,503 | 2/1978 | Atwood et al. ....................... | 23/259 |
| 4,111,051 | 9/1978 | Tamm et al. ........................... | 73/423 A |
| 4,131,426 | 12/1978 | Range ..................................... | 141/1 |
| 4,210,724 | 7/1980 | Sogi et al. ............................. | 435/292 |
| 4,217,780 | 8/1980 | O'Connell et al. ................... | 73/421 |
| 4,338,280 | 7/1982 | Ambers et al. ....................... | 422/68 |
| 4,361,540 | 11/1982 | Weinberg et al. .................... | 422/68 |

Primary Examiner—Barry S. Richman
Assistant Examiner—Michael S. Gzybowski

[57] ABSTRACT

Liquid sampling apparatus includes a hollow sample intake tube that has an inlet port adapted to receive sample material to be analyzed, and is mounted on a support for movement about a fixed pivot between a reset position and at least two sample intake positions. Also mounted on the support is manually manipulable drive link structure that carries a slider assembly that receives the intake tube. Track structure on the support guides movement of the link structure to slide the slide member along the intake tube between a reset position in which the inlet port is aligned with a waste receptacle, a first sample in which the inlet port extends forward of the slide assembly for insertion into a sample container, and a second sample in which the inlet port is housed in coupling structure carried by the slider assembly and presented to the operator for connection of a transfer device such as a capillary tube.

18 Claims, 10 Drawing Figures

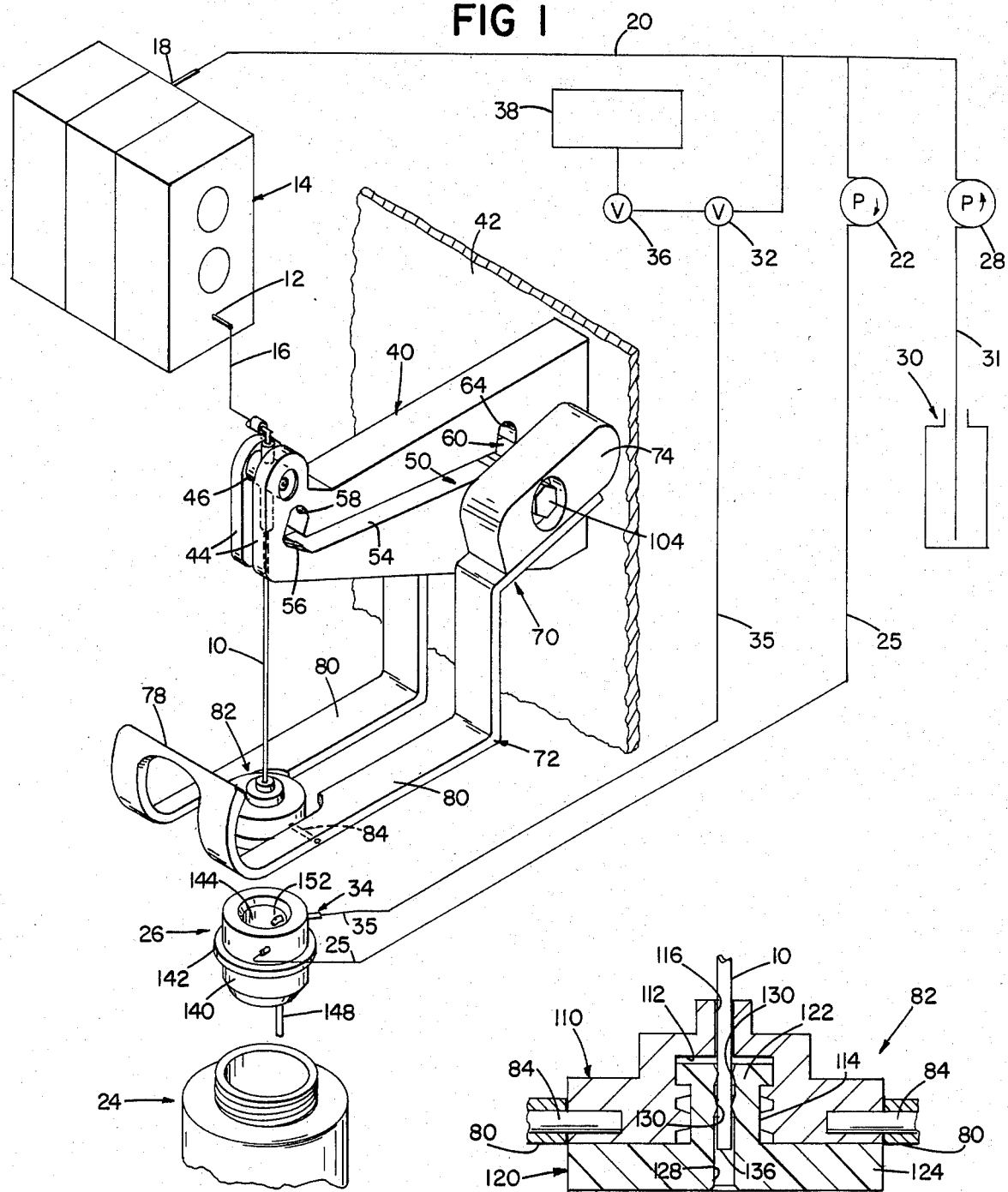

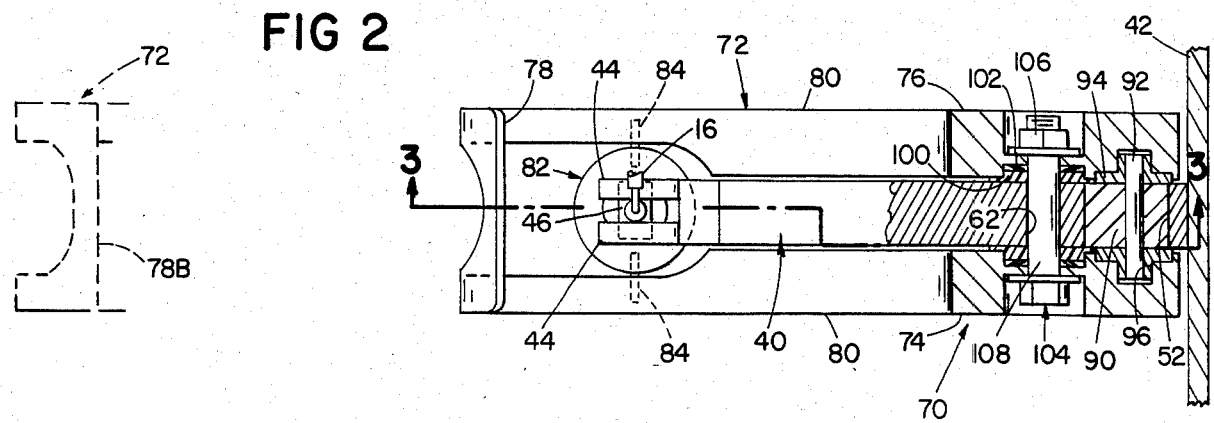
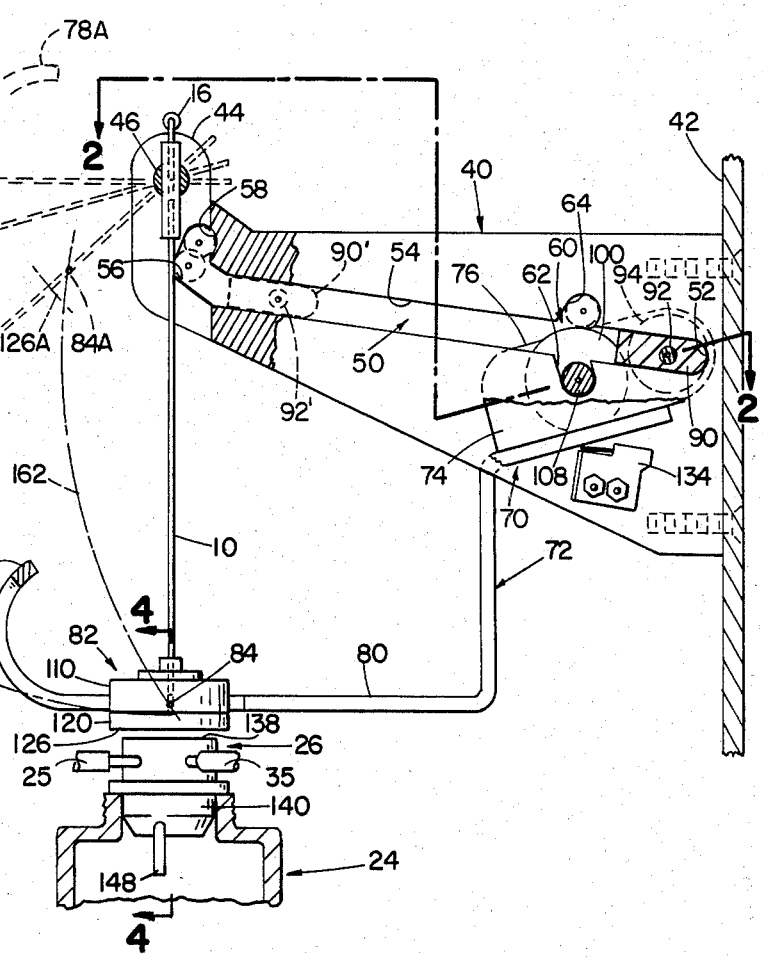

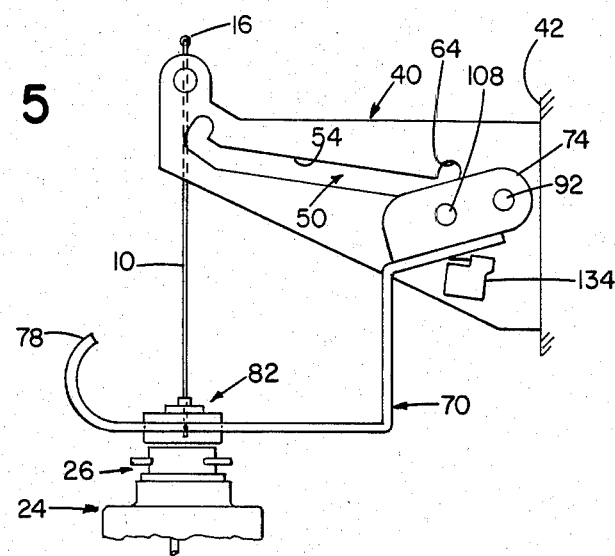
FIG 5
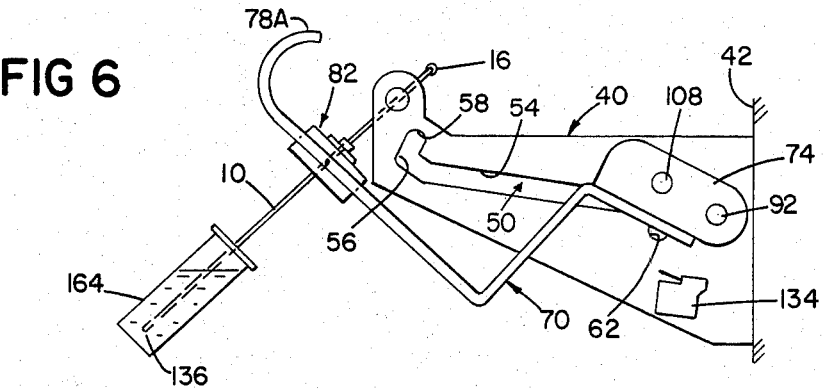
FIG 6
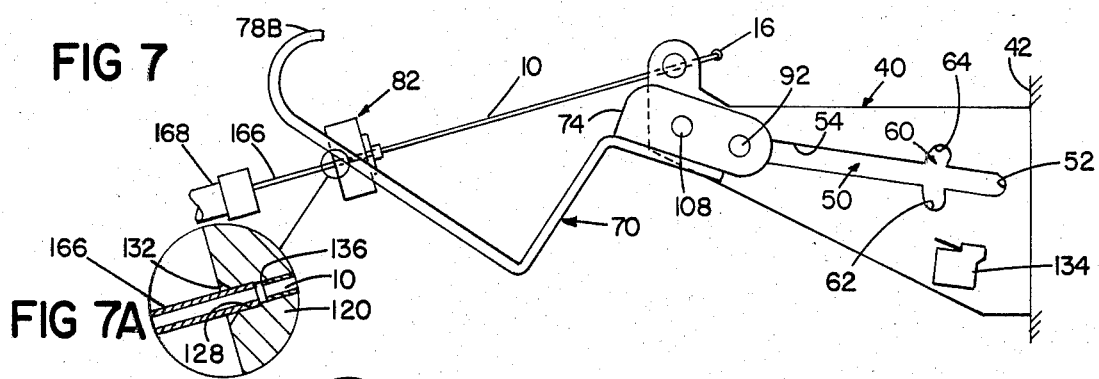
FIG 7
FIG 7A
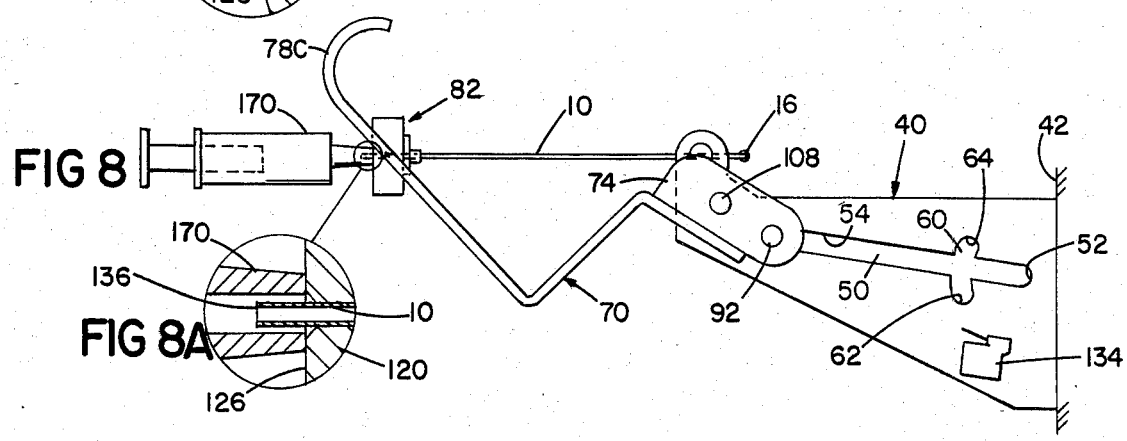
FIG 8
FIG 8A

FLUID SAMPLING

This invention relates to fluid sampling and more particularly to sampler mechanisms type that are useful in clinical analysis systems.

Need exists in many fields for efficient and reliable sampler mechanisms capable of rapidly obtaining successive fluid samples to be analyzed without cross-contamination or intermixing between successive samples. One such field is clinical analysis where economics and cost effectiveness encourage nearly continuous operation with samples of biological fluids from different patients being analyzed in rapid succession. Liquid samples to be analyzed may be presented by various devices such as sample vessels, micropipettes and syringes—for syringe injecting and capillary aspirating as well as aspirating samples from containers. The sampler mechanism preferably is adapted for operation by relatively unskilled persons and is operable in distinct modes to permit introduction of sample into the analyzer from various sources. Also, the intake device should be easily and effectively cleaned to remove sample residue from the intake device and avoid problems of cross-contamination which could result in inaccurate data and incorrect analysis.

In accordance with the invention there is provided liquid sampling apparatus that includes a hollow sample intake tube having an inlet port adapted to receive sample material to be analyzed, the intake tube being mounted on a support and movable about a fixed pivot between a reset position and at least two sample intake positions. Also mounted on the support is manually manipulable drive link structure that is coupled to the support and carries a slider assembly that receives the intake tube. Track structure on the support guides movement of the link structure to slide the slider assembly along the intake tube between a reset position in which the inlet port is aligned with a waste receptacle, a first sample position in which the inlet port extends forward of the slider assembly for insertion into a sample container, and a second sample position in which the inlet port is housed in coupling structure carried by the slider assembly and presented to the operator for connection of a transfer device such as a capillary tube.

In a particular embodiment, the apparatus includes an analysis chamber adapted to receive sample material to be analyzed, sensor means coupled to said analysis chamber for providing an output signal related to a constituent of the sample material, and the intake tube (of stainless steel and with an inner diameter of less than one millimeter) is connected to the analysis chamber inlet. The slider assembly includes a seal member of resilient material that has a through passage in which the intake tube is disposed and an end surface with a socket adapted to receive a capillary tube. The drive link structure includes a pivot connection to the support and is rotatable about a first pivot to expose the inlet port and is translatable along the track to a second position in which the coupling member may be moved relative to the inlet port between a first position in which the port is housed and a second position in which the port extends beyond the coupling surface so that a syringe may be aligned with the inlet port and sample may be introduced by syringe injection rather than by aspiration. Resilient clutch structure holds the link structure in each of the sample positions.

A sensor element senses the intake of a microsample of the material to be analyzed, and pump means (which may be separate or combined units) connected to the analysis chamber is driven in a first mode for drawing sample into the system and in a second mode for flowing cleaning liquid through the analysis chamber and the intake path in a backflushing action. Rinse apparatus that includes an adapter in communication with a waste system, a spray nozzle, and a valved control arrangement controls flow of cleaning fluid to the nozzle. The valve arrangement also bypasses the pump means in an inject mode of sample introduction. The sampler apparatus is movable by the operator to a sample introduction position in which a microsample is drawn into the analyzer. As soon as intake of the microsample is complete, the operator returns the sampler to reset condition in communication with a waste container and the analyzer then performs a sample analysis and flushing sequence. The invention provides an improved sampler mechanism that is easy to operate, provides convenient intake of microsamples from a variety of transfer devices, and minimizes cross-contamination between successive samples.

Other features and advantages of the invention will be seen as the following description of a particular embodiment progresses, in conjunction with the drawings, in which:

FIG. 1 is a diagrammatic view of a blood gas analysis system, including a perspective view of sampler apparatus in accordance with the invention;

FIG. 2 is a top plan view of the sampler apparatus, with a portion in section taken along the line 2—2 of FIG. 3;

FIG. 3 is a sectional view taken along the line 3—3 of FIG. 2, together with diagrammatic indications of movements of the sampler mechanism;

FIG. 4 is a sectional view, taken along the line 4—4 of FIG. 3 and on an enlarged scale, of the slider and rinse assemblies; and FIGS. 5–8 are diagrams indicating a series of operative positions of the sampler apparatus shown in FIG. 1.

DESCRIPTION OF PARTICULAR EMBODIMENT

Shown in FIG. 1 in diagrammatic form are portions of a blood gas analysis system that incorporates sampler apparatus in accordance with the invention, the sampler apparatus being shown in perspective view. That sampler apparatus includes a stainless steel inlet tube 10 that has a length of about ten centimeters, an outer diameter of about one millimeter, and an inner diameter of about 0.8 millimeter. Connected between the outlet of tube 10 and inlet port 12 of analysis chamber module 14 is a transfer tube 16. The outlet port 18 of analysis chamber module 16 is connected via tubing 20 to a peristaltic pump 22 that is connected to waste container 24 via line 25 and adapter 26; a second peristaltic pump 28 that is connected to flush solution reservoir 30 via line 31; a bypass valve 32 that is connected to spray nozzle 34 in adapter 36 via line 35; and control valve 36 that is connected to gas pressure (five psi) sources 38. Further details of module 14 may be had with reference to copending application Ser. No. 319,314 filed Nov. 9, 1981, entitled Analysis System, which application is assigned to the same assignee as this application and is expressly incorporated herein by reference.

The sampler apparatus includes support arm 40 that is mounted on and projects forwardly from the face plate 42 of the analyzer. At the forward end of arm 40 are two spaced walls 44 which define a recess in which intake tube 10 is supported on transversely extending pivot shaft 46. Formed in support arm 40 is track structure that includes guide channel 50 that has a reset end 52 (FIG. 3), a straight or translational portion 54 that extends from reset end 52 to a first operative end recess 56 with a second operative recess 58 above recess 56; and an intersecting arcuate track 60 that has a lower reset recess 62 and an upper operative recess 64.

Drive link assembly 70 is guided for movement along tracks 50 and 60 and has a link member 72 with one end secured to clutch blocks 74, 76 on either side of arm 40, with an upturned handle portion 78 at its forward end and with two intermediate spaced arms 80 between which slider assembly 82 is supported by roll pins 84.

Further details of the sampler mechanism may be seen with reference to FIGS. 2 and 3. Support arm 40 has a width of about one centimeter, a length of about eleven centimeters, and a vertical height of about five centimeters. Translational track 50 has a width of about ½ centimeter and a length of about nine centimeters. Arcuate track 60 allows rotation of the drive assembly through an angle of about 30 degrees. Drive assembly 70 includes a slide block 90 through which pivot pin 92 extends and that is journalled in bushings 94, 96 that in turn are carried by slide blocks 74, 76. Each slide block 74, 76 has a recess which receives a Teflon clutch disc 100 and a spring washer 102 that are secured by clamp bolt 104 that extends through guide track 50 and slide blocks 74, 76 and is secured with lock type nut 106. The frictional positioning force of discs 100 is maintained by spring washers 102. As indicated in FIG. 3, slide block 90 has a dimension corresponding to the width of track 50 and the shank 108 of clamp bolt 104 has a diameter corresponding to the width of translational track 50 and of arcuate track 60.

Further details of the adapter 26 and the slider assembly 82 may be had with reference to FIG. 4. Slider assembly 82 includes a body member 110 is about 2.5 centimeters in diameter and one centimeter in overall height. Formed in body member 110 is a recess 112 that has dual acme threads 114 along its wall and an aligned passage 116 that has a diameter slightly greater than one millimeter. Received in recess 112 is a wiper seal insert 120 of molded silicone rubber (of about 50 Shore A durometer) that has a coupling portion 122 disposed in recess 112 and a flange portion 124 that is seated against the lower face of body 112. Its flat planar surface 126 is about 2.3 centimeters in diameter and its through passage 128 of about 1.2 millimeter diameter is aligned with through passage 116. Formed in passage 128 are wiper projections 130 that each define a passage restriction of about ¾ millimeter diameter. The entrance end 132 of passage 128 is flared at an angle of 45 degrees and passage 128 has a length of about one centimeter. When intake tube 10 is in its vertical or reset position, as indicated by a signal from microswitch 134 (FIG. 3), surface 126 of seal member 120 is disposed over and effectively closes the top opening 138 of waste bottle adapter 26 and inlet port 136 is housed in wiper 120.

Adapter 26 is received in the top opening of waste bottle 24 and has a cylindrical body member 140 (about two centimeters in diameter and about two centimeters in length) with flange 142 that is seated on the top surface of waste bottle 24. Body 140 has a through passage 144 (about 1.1 centimeters in diameter) with a flared upper portion 146 that defines top opening 138. Stainless steel waste tube 148 is connected to waste line 25. Stainless steel nozzle tube 34 is connected to flush line 35, is plugged at end 150 and has a spray orifice 152 through which spray 154 flows for impingement on entrance surfaces 132 of seal insert 120 and on housed tip 136 of intake tube 10 during the flush sequence.

The drive link assembly 70 is movable along track 50 in a translational direction and along track 60 in a rotational direction. Slider assembly 82 is carried by the link assembly 70 and pivots on roll pins 84 and slides along intake tube 10. Inlet port 136 of intake tube 10, which is housed in seal member 120 with the sampler mechanism is in its reset position as indicated in FIG. 4, rotates about the axis of support shaft 46 along a path 160 as indicated in FIG. 3. With the drive assembly in its rearward position in track 50 (so that slide block 90 is seated in the track end 52), lifting of handle 78 rotates the slide assembly 82 along path 162 and when bolt shank 108 is seated in upper recess 64 of the arcuate track, the roll pins axis is at point 84A, the intake tube 10 in position 10A, the inlet port is at position 136A, and the seal surface is at 126A.

In a second (translational) mode of operation, the drive assembly may be slid along track 50 to position pivot pin 92 at point 92' with bolt shank 108 seated in recess 56. That action rotates intake tube 10 to the position 10B with its inlet port 136 housed in seal member 120. Raising handle 78 from that position rotates tube 10 up to generally horizontal position 10C in which the tube inlet port is at position 136C and projects about four millimeters beyond surface 126 (position 126C).

The sampler reset position is diagrammatically shown in FIG. 5, bolt shank 108 being seated in recess 62, tube 10 being in vertical position with its inlet port 136 housed in seal member 120, and seal surface 126 directly over and essentially closing the top port of adapter 26, this reset position being signalled by microswitch 134.

When the operator desires to aspirate liquid to be analyzed from container 164, handle 78 is raised to the position 78A shown in FIG. 6, moving bolt shank 108 along the arcuate track 60 to seat in the upper recess 64 as indicated in FIG. 6. This movement slides assembly 82 along intake tube 10 to expose about a six centimeter length of tube 10 as indicated in FIG. 6. The operator inserts inlet port 136 into sample container 164 and depresses an analyzer "enter" key which causes the system controller to energize peristaltic pump 22 to rotate in the direction indicated in FIG. 1 and create reduced pressure in intake tube 10 that draws sample from container 164 into the sample flow path. When the system indicates that a desired sample volume (65 microliters in a particular embodiment) has been aspirated from container 164, pump 22 is deenergized and the controller signals the intake of the predetermined volume of microsample by energizing an indicator in response to which the operator withdraws the sample container 164 and returns the sampler mechanism to the reset position shown in FIG. 5, closing switch 134. After analysis, pump 28 is energized by the controller and flush solution is flowed back from container 30 back through the sample module 14 and inlet tube 10 into the waste bottle 24 to clean the sample path. During the flush sequence, valve 32 is briefly operated (three seconds) to connect lines 20 and 35 and prime line 35 with flush solution. After pump 28 is deenergized, the controller opens valve 36 (for five seconds) to connect five psi gas pressure source 38 through valve 32 to line 35, producing a spray 156 of flush solution that rinses off the seal passage 132 and aspiration tube 10 followed by a spray of gas that removes excess cleaning solution from surfaces of seal member 120 and tube 10, thus preparing the system for intake of the next sample.

In a second mode of operation illustrated in FIG. 7, the operator lifts the sampler handle 78 to an intermediate position and then pulls the drive assembly forward, sliding bolt 104 and slide block 90 along track 54 until shank 108 is seated in recess 56 (handle position 78B). In that position, the inlet port 136 is housed within seal member 120, as indicated in FIG. 7A, and the operator inserts a capillary transfer tube 166 into socket 128 and attaches a micropipette 168. In response to an enter command, the system controller operates pump 22 to aspirate sample from pipette 168. When aspiration of the predetermined microsample volume is sensed by the system, the operator removes the capillary tube 164 and returns the sampler unit to its reset position of FIG. 5, again signalled by microswitch 134. The analyzer then analyzes the sample and backflushes the sample path and cleans the seal member 120 as previously described.

In a third mode of operation (inject), the operator raises the sampler handle 78 from the FIG. 7 position to the FIG. 8 position (78C), rotating the assembly upward, which movement places the inlet tube 10 in a substantially horizontal position and moves the slider assembly 82 rearwardly so that about a four millimeter length of sample tube 10 projects beyond the plane of seal surface 126 as indicated in FIG. 8A. The operator then seats the tip of a syringe 170 (or other injection device as a Douglass of similar gas bag) on seal surface 126 with port 136 of inlet tube 10 extending into the throat of the syringe 170. The pressing action of the injection device 170 against seal surface 126 enhances sealing of the sample transfer passage. In response to depression of an "inject" key, the system controller opens the bypass valve 32 so that the outlet 18 of analysis module 14 is connected to the waste bottle 24. The operator then injects the sample into intake tube 10. When injection of the predetermined microsample volume is indicated by the sensor, the operator removes the injection syringe 170 and returns the sampler apparatus to its reset position in FIG. 5. When the sampler reaches that reset position (as indicated by microswitch 134), the analyzer controller moves the microsample into the analysis module 14, an analysis is performed, and then the analysis module and sample inlet tube are cleaned as previously described.

While a particular embodiment of the invention has been shown and described, various modifications thereof will be apparent to those skilled in the art, and therefore it is not intended that the invention be limited to the disclosed embodiment or to details thereof, and departures may be made therefrom within the spirit and scope of the invention.

What is claimed is:

1. Liquid sample analyzer apparatus having an analysis chamber adapted to receive sample material to be analyzed, sensor means coupled to said analysis chamber for providing an output signal related to a constituent of the sample material,
  sampling apparatus comprising a hollow sample intake tube having an inlet port adapted to receive sample material to be analyzed and an outlet port coupled to said analysis chamber,
  slider structure that receives said intake tube,
  support structure including tube support structure and track structure in predetermined fixed relation to said tube support structure,
  means mounting said intake tube on said tube support structure for movement between a reset position and at least two sample intake positions,
  manually manipulable drive link structure having a first portion mounted on said track structure for movement along said track structure and a second portion spaced from said first portion, said slider structure being pivotably mounted on and carried by said second portion,
  said first portion of said link structure being movable along said track structure to cause said second portion to produce guiding movement of said slider structure to move said intake tube between said reset position in which said inlet port is aligned with a waste receptacle, a first sample position in which said inlet port extends forward of said slider structure and is presented to an operator for insertion into a sample container, and a second sample position in which said inlet port is housed in said slider structure and presented to an operator for connection of a transfer device such as a capillary tube,
  and a sampling apparatus control arrangement including
  means for flowing sample material through said sample inlet port into said analysis chamber, and
  means for flowing cleaning fluid through said analysis chamber and said sampling apparatus in a flushing action.

2. The apparatus of claim 1 and further including rinse apparatus for directing a flow of cleaning fluid against a surface of said slider structure when said intake tube is in said reset position for removing sample residue from said slider structure.

3. The apparatus of claim 2 wherein said rinse apparatus includes an adapter in communication with said waste receptacle, and a spray orifice, and said control arrangement includes valve means for controlling flow of cleaning fluid to said orifice.

4. The apparatus of claim 3 wherein said control arrangement includes pump means connected to said analysis chamber, and said sample material flowing means and said cleaning fluid flowing means include means to drive said pump means in a first mode for drawing sample into said analysis chamber and in a second mode for flowing cleaning liquid through said analysis chamber and said intake tube in a back flushing action.

5. The apparatus of claim 4 and further including a valve arrangement connected between said analysis chamber and said pump drive means, said valve arrangement having a first condition venting said analysis chamber and a second condition connecting a source of gas pressure to said rinse apparatus.

6. The apparatus of either claim 1 or 5 wherein said link structure has a rotational movement mode along said track structure for moving said intake port to one of said sample positions and a translational movement mode along said track structure for moving said intake port to the other of said sample positions.

7. The apparatus of claim 6 wherein said link structure includes a rigid member that has a connection to said track structure at one end, a handle portion at its opposite end, and said second portion is located between said ends.

8. The apparatus of claim 7 wherein said link structure further includes resilient clutch structure for holding said rigid member in each of said sample positions.

9. The apparatus of claim 8 wherein said intake tube is of metal, is pivotably connected to said tube support structure and has an inner diameter of less than one millimeter, and said slider structure includes a seal member of resilient material that has a through passage in which said intake tube is disposed and an end surface with a socket adapted to receive a capillary tube.

10. Liquid sampling apparatus comprising
a hollow sample intake tube having an inlet port adapted to receive sample material to be analyzed,
support structure including track structure, said intake tube being pivotably mounted on said support structure for movement about a fixed pivot between a reset position and at least two sample intake positions,
manually manipulable drive link structure mounted on said support structure and including first and second portions and a handle portion,
slider structure pivotably mounted on and carried by said second portion of said link structure and having a through passage in which said intake tube is received,
said first portion of said link structure being movable along said track structure for guiding movement of said link structure to move said slider structure along said intake tube between a reset position in which said inlet port is aligned with a waste receptacle, a first sample position in which said inlet port extends forward of said slider structure and is presented to an operator for insertion into a sample container, and a second sample position in which said inlet port is housed in said slider structure, and presented to an operator for connection of a transfer device such as a capillary tube.

11. The apparatus of claim 10 wherein said link structure has a rotational movement mode along said track structure for moving said intake port to one of said sample positions and a translational movement mode along said track structure for moving said intake port to the other of said sample positions.

12. The apparatus of claim 11 and further including resilient clutch structure for holding said link structure in each of said sample positions.

13. The apparatus of either claim 10 or 11 wherein said intake tube is of metal and has an inner diameter of less than one millimeter, and said slider structure includes a seal member of resilient material that has a through passage in which the intake tube is disposed.

14. The apparatus of claim 13 wherein said seal member has an end surface with a socket adapted to receive a capillary tube.

15. The apparatus of either claim 1, 5 or 10 wherein said track structure includes a slot in said support structure, said drive link structure includes a slide member disposed in said slot, said slide member including a pivot connection to said support structure and said drive link structure being rotatable about said slide member pivot connection to move said slider structure along said inlet tube and expose said inlet port and translatable along said slot to a second position in which said slider structure may be moved relative to said inlet port between a first condition in which said port is housed and a second condition in which said inlet port is disposed forward of the end surface of said slider structure.

16. The apparatus of claim 15 wherein said drive link structure includes a resiliently biased clutch mechanism that cooperates with said support structure.

17. The apparatus of claim 15 and further including rinse apparatus for directing a flow of cleaning fluid against a surface of said slider structure for removing sample residue from said slider structure.

18. The apparatus of claim 17 wherein said rinse apparatus includes an adapter in communication with a waste system, a spray orifice carried by said adapter, said slider structure being aligned with said adapter in said reset position, valve means for controlling flow of cleaning fluid to said orifice, and interlock means for enabling said valve means when said intake tube is in said reset position.

* * * * *